United States Patent
Fini et al.

(10) Patent No.: US 11,577,007 B2
(45) Date of Patent: Feb. 14, 2023

(54) TUBE CONNECTION

(71) Applicant: FRESENIUS MEDICAL CARE DEUTSCHLAND GMBH, Bad Homburg (DE)

(72) Inventors: Massimo Fini, Mirandola (IT); Martin Lauer, St. Wendel (DE); Reinhold Reiter, Crema (IT); Alain Veneroni, Spino d'Adda (IT)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 1122 days.

(21) Appl. No.: 16/302,136

(22) PCT Filed: May 19, 2017

(86) PCT No.: PCT/EP2017/062114
§ 371 (c)(1),
(2) Date: Nov. 16, 2018

(87) PCT Pub. No.: WO2017/198822
PCT Pub. Date: Nov. 23, 2017

(65) Prior Publication Data
US 2020/0306416 A1 Oct. 1, 2020

(30) Foreign Application Priority Data
May 20, 2016 (EP) ..................................... 16001168

(51) Int. Cl.
*A61M 39/12* (2006.01)
*A61L 29/04* (2006.01)
*A61L 29/14* (2006.01)

(52) U.S. Cl.
CPC ........... *A61L 29/049* (2013.01); *A61L 29/141* (2013.01); *A61M 39/12* (2013.01)

(58) Field of Classification Search
CPC . A61M 39/12; A61M 25/0014; A61L 29/049; A61L 29/141
See application file for complete search history.

(56) References Cited

U.S. PATENT DOCUMENTS 4,256,333 A * 3/1981 Jones .................... A61M 39/12
285/915
4,417,753 A * 11/1983 Bacehowski ........... F16L 47/02
285/423

(Continued)

FOREIGN PATENT DOCUMENTS

DE 102005024621 A1 12/2006
JP 2005218649 A 8/2005

(Continued)

OTHER PUBLICATIONS

International Search Report issued in corresponding International Patent Application No. PCT/EP2017/062114 (with English translation) dated Aug. 21, 2017 (4 pages).

*Primary Examiner* — David Bochna
(74) *Attorney, Agent, or Firm* — Kilyk & Bowersox, P.L.L.C.

(57) ABSTRACT

A tube connection part adapted to accommodate a flexible tube made from a material comprising polyvinyl chloride, wherein said tube connection part comprises a sleeve adapted to form an overlapping region between said tube connection part and said tube, wherein an adhesion promoting agent is deposited on at least a subsection of a surface of said sleeve, characterized in that the adhesion promoting agent comprises a styrene-butadiene block copolymer.

14 Claims, 5 Drawing Sheets

(56) References Cited

U.S. PATENT DOCUMENTS

| | | | |
|---|---|---|---|
| 4,687,474 A * | 8/1987 | Takanashi | A61M 39/12 604/257 |
| 6,303,200 B1 * | 10/2001 | Woo | A61L 29/049 525/98 |
| 2004/0059063 A1 | 3/2004 | Yang et al. | |
| 2004/0155457 A1 * | 8/2004 | Mejlhede | A61M 39/12 285/285.1 |
| 2008/0287843 A1 * | 11/2008 | Mros | A61M 39/12 601/152 |
| 2009/0051160 A1 * | 2/2009 | Kanner | A61M 39/12 285/24 |
| 2009/0299260 A1 | 12/2009 | Kreischer et al. | |
| 2010/0270230 A1 | 10/2010 | Brueckner et al. | |
| 2010/0274168 A1 * | 10/2010 | Gronau | A61M 1/3621 604/4.01 |
| 2013/0123739 A1 * | 5/2013 | Yoshikawa | A61L 29/085 604/408 |
| 2014/0091569 A1 * | 4/2014 | Spohn | A61M 39/12 285/285.1 |
| 2015/0345674 A1 * | 12/2015 | Coulson | A61M 39/12 285/417 |
| 2016/0106961 A1 | 4/2016 | Broyles et al. | |
| 2016/0265698 A1 * | 9/2016 | Cai | A61M 39/12 |
| 2016/0305577 A1 * | 10/2016 | Huschke | A61M 39/12 |
| 2016/0305582 A1 * | 10/2016 | Blomberg | A61M 39/12 |
| 2019/0001026 A1 * | 1/2019 | Sandford | A61L 29/141 |
| 2021/0048127 A1 * | 2/2021 | Zumbrum | A61M 39/12 |

FOREIGN PATENT DOCUMENTS

| | | |
|---|---|---|
| JP | 2006130144 A | 5/2006 |
| WO | 8300699 | 3/1983 |

\* cited by examiner

TUBE CONNECTION

This application is a National Stage Application of PCT/EP2017/062114, filed May 19, 2017, which claims priority to European Patent Application No. 16001168.0, filed May 20, 2016.

FIELD OF THE INVENTION

This invention relates to a novel tube connection between a tube connection part and a flexible tube, said flexible tube, and a fluid processing cassette module with tube connection parts being made from a material comprising polypropylene and a flexible tube made from a material comprising polyvinyl chloride by interposing an adhesion promoting agent which comprises styrene-butadiene block copolymer.

BACKGROUND OF THE INVENTION

Connection of flexible tubing to corresponding connecting parts has ever since been a challenging issue throughout development and production of medical devices. In several fields of medical engineering as presented for example by Infusion, clinical nutrition, dialysis, transfusion or ophthalmic surgery, and others to name only a few, patient care is not conceivable without the use of a safe and reliable flexible tubing carrying therapeutic or bodily fluids for respective therapeutic purposes.

In this respect polyvinyl chloride (hereinafter called PVC) has been widely used as a most promising material fulfilling the requirements from the medical sight as well as providing outstanding material properties which makes PVC suitable for the production of medical tubes. Hence PVC is a commonly envisioned material in the production of medical disposable devices.

Nevertheless several crucial problems arise from the use of PVC in medical disposables, such as tubes. The PVC material itself has to be modified by plasticizers to obtain the required material properties, which makes PVC suitable for the production of tubing or films. In this respect plasticizing of PVC is believed to cause a partial dissolution of the PVC material which in consequence provides high quality tube products especially in respect of resilience and kinking resistance.

On the other hand, PVC materials suffer from the drawback of plasticizer bleeding. Over time the plasticizer elutes from the PVC material and can contaminate bodily or therapeutic fluids which come in contact with the PVC material by using for example a PVC medical disposable during a therapeutic treatment session. A further drawback has to be seen in the fact that PVC is not compatible with several other plastic materials, e.g. polypropylene and other polyolefins, which are often used in the manufacturing of medical disposables. Incompatibility in this respect means that there is only a low interaction tendency of PVC with another plastic material in attempts to form a connection, for example by welding or gluing. However, a material interaction tendency is necessary when PVC and a second material shall form joints like tube connections. In the referred case PVC and polypropylene show such a low interaction tendency that a connection between a PVC tube and a polypropylene connection part is not staple by joining processes like welding, gluing or blocking. Without any auxiliary means any such connection is by far not resilient enough to meet the requirements of medical disposables.

In respect of these drawbacks tendencies appeared to sort out PVC materials from the manufacturing of medical disposables. In this respect tubes made from polyolefin were developed to provide a substitution for PVC tubing to solve the problem of the inferior compatibility to PP (for example EP 2 001 670). However, those tubes are problematic in respect of kinking resistance, resilience and increased material and production costs.

Other attempts were made to find solutions whereupon PVC tubing might form resilient connections to commonly used PVC incompatible plastic materials like PP. In this respect DE 10 2005 024 621 shows a concept wherein a PVC tube might be connected to a tube part and resilience of the tube connection is achieved by a heat shrink tube which is wrapped over an overlapping region of the PVC tube and the rigid connecting part to form a force fit tube connection.

U.S. Pat. No. 4,417,753 suggests to use a poly(ethyl-vinyl acetate) (EVA) material which is susceptible to radio frequency irradiation and which heats up to form a connection between a PVC connection part and another connection part.

Solutions reported in the state of the art still are so far not sufficient in respect of required quality performances of medical disposables especially in regard of fluid processing cassettes modules which are recently used in dialysis therapy (for example WO 2010/121819).

Fluid processing cassette modules are used for the processing of therapeutic or bodily fluids during a therapeutical treatment session. Such cassettes are connected with respective tubing for conveying respective fluids to and from the fluid processing cassette module via tube connection parts. The tube connection parts can be produced from different materials, PP being the preferred and commonly accepted material. It is well established to form resilient joints between a tube connection part of the cassette and the tubing by using compatible materials like PP for the cassette and polyolefin materials for tubes. In this case the cassette module and the tubing comprise a compatible material, which enables the formation of weldable joints. When switching to PVC materials it is found that is impossible to form resilient joints between a PP tube seat, i.e. a tube connection part on the cassette, and PVC tubing because of the low material interaction tendency. One option to obtain said joints is to find appropriate auxiliary means which would support the gluing of the respective parts.

A basic requirement for gluing PVC to PP is therefore to provide an adhesion promoter that makes PP and PVC compatible in a joint region. In addition resilience of a tube connection between aforementioned fluid processing cassette modules and respective tubing has to fulfill outstanding challenges in respect of tensile and torsional strength. This comes from the fact that a fluid processing cassette module is normally fixedly engaged in corresponding receiving sections of a dialysis machine, or other therapeutic machines, wherein the tubing is flexible and loosely movable, hanging down from the fixedly engaged cassette. As a consequence movements of the tubing will steadily initiate tensile and torsional stress directly on the joint region between flexible tube and tube connecting part of the cassette which increases the danger that respective tubes will detach out of the tube connection. This situation is aggravated by the problem to join pump tube sections to connection parts placed on the fluid processing cassette module. Those pump tubes sections are steadily forced under tensile and torsional stress by the respective roller pump actor to maintain a desired fluid flow. Those stress actions are immediately initiated to the tube connection region where the respective pump tube sections may peel or rupture out of their joint.

The glued joint region has to fulfill further requirements like thermostability. Preferred sterilization methods for medical devices making use of raised temperature induced sterilization. Examples are the vacuum-steam sterilization or sterilization by autoclave.

OBJECTS OF THE INVENTION

In regard of the aforementioned problems it is an object of the invention to provide a tube connection part which provides a resilient joint in an overlapping region between the tube connecting part and flexible tubing made from PVC material.

In particular it was a further object of the invention to provide an assembly of a tube connection part and a flexible tube made from a material comprising polyvinyl chloride, whereby the tube connection part and said flexible tube form a resilient joint in an overlapping connecting region.

In particular it was a further object of the invention to provide a fluid processing cassette module for processing therapeutic or bodily fluids comprising at least on tube connection part capable to form resilient joints in an overlapping connection region with a flexible tube made from a material comprising polyvinyl chloride.

In particular it was a further object of the invention to provide a tube made from a PVC material which is capable to form resilient joints in an overlapping region with a tube connection.

In particular it was a further object of the invention to provide an assembly comprising a fluid processing cassette module for processing therapeutic or bodily fluids comprising a tube connection part and a flexible tube made from a material comprising polyvinyl chloride.

SUMMARY OF THE INVENTION

Surprisingly it has been found that in a first aspect of the invention the problem according to an aforementioned object of the invention is solved by a tube connection part which is adapted to accommodate a flexible tube made from a material comprising polyvinyl chloride and which comprises a sleeve adapted to form an overlapping region between said tube connection part and said tube, wherein an adhesion promoting agent is deposited on at least a subsection of a surface of said sleeve, wherein the adhesion promoting material comprises a styrene-butadiene block copolymer.

In a further embodiment of a first aspect of the invention the tube connection part is characterized in that the sleeve comprises protruding ribs which extend in axial direction thereof preferably in axial direction within a part or the total of the overlapping region.

In a further embodiment of a first aspect of the invention the tube connection part is characterized in that the protruding ribs are dove tail shaped.

In a further embodiment of a first aspect of the invention the tube connection part is characterized in that said sleeve comprises at least one recess extending inwardly from its outer surface.

In a further embodiment of a first aspect of the invention the tube connection part is characterized in that the adhesion promoting agent is deposited as an overmolding on at least a subsection of a surface of said sleeve.

In a further embodiment of a first aspect of the invention the tube connection part is characterized in that said adhesion promoting agent forms an outer collar on said sleeve of the tube connection.

In a further embodiment of a first aspect of the invention the tube connection is characterized in that at least a portion of said adhesion promoting agent forms a front surface flange adapted to accommodate an end face of said tube.

In a further embodiment of a first aspect of the invention the tube connection part is characterized in that the overall styrene content in said styrene-butadiene block copolymer amounts 20% to 80% by weight, preferably 25% to 75% by weight, more preferably 40% to 70% by weight.

In a further embodiment of a first aspect of the invention the tube connection part is characterized in that the styrene-butadiene block copolymer exhibits an Order-Disorder-Transition Temperature of above 140° C. and up to 220° C., or a Shore A hardness in the range of 80 or 90, or exhibits an Order-Disorder Transition temperature and a Shore A hardness, as respectively defined hereinbefore.

In a further embodiment of a first aspect of the invention the tube connection part is characterized in that the sleeve forms a female or a male connecting part.

In a further embodiment of a first aspect of the invention the tube connection part is characterized in that it is made of a plastic material, or is rigid, or is rigid and made of a plastic material, wherein said plastic material comprises or consists of polypropylene.

In a second aspect of the invention it has been found that the problem according to an aforementioned object of the invention is solved by an assembly comprising the tube connection part according to any embodiment of the first aspect of the invention and a flexible tube made from a material comprising polyvinyl chloride, wherein said tube is engaged in the overlapping region of said sleeve of the tube connection part, and wherein said tube is connected to said tube connection part via said adhesion promoting material.

In a further embodiment of the second aspect of the invention said assembly is characterized in that the flexible tube is made from a material comprising polyvinyl chloride which comprises a plasticizer chosen from the group of alkyl esters of trimellic acid, terephthalic acid or phtalic acid preferably the plasticizer is chosen from a trioctyl trimellitate, dioctyl terephthalate or dioctylphtalate.

In a third aspect of the invention it has been found that the problem according to an aforementioned object of the invention is solved by a fluid processing cassette module for processing therapeutic or bodily fluids comprising at least one tube connection part according to any embodiment of the second aspect of the invention or an assembly according to the third aspect of the invention.

In a further embodiment of the third aspect the fluid processing cassette module comprises a plurality of tube connection parts characterized in that at least two tube connection parts are interconnected by at least one conduit adapted to simultaneously distribute a polymer melt stream to the at least two rigid connecting parts.

In a fourth aspect of the invention it has been found that the problem according to an aforementioned object of the invention is solved by a flexible tube made from a material comprising polyvinyl chloride which is fully or in part superimposed by a adhesion promoting agent comprising a styrene-butadiene block copolymer.

In a further embodiment of the fourth aspect of the invention said flexible tube is characterized in that the adhesion promoting agent comprising styrene-butadiene block copolymer is applied to a part or the total of an outer surface of said tube.

In a further embodiment of the fourth aspect of the invention said flexible tube is characterized in that the adhesion promoting agent comprising styrene-butadiene block copolymer is applied to a part or the total of an outer surface of said tube.

In a further embodiment of the fourth aspect of the invention said flexible tube is characterized in that the continuous layer of said adhesion promoting agent/styrene-butadiene block copolymer and said tube are made by coextrusion.

In a further embodiment of the fourth aspect of the invention said flexible tube is characterized in that the continuous layer is in the form of a bushing applied to an end section of said tube.

In a further embodiment of the fourth aspect of the invention said flexible tube is characterized in that the continuous layer of the connection mediating material is applied by printing.

In a further embodiment of the fourth aspect of the invention said flexible tube is characterized in that the polyvinyl chloride material comprises a plasticizer chosen from the group of alkyl esters of trimellic acid, terephtalic acid or phtalic acid, preferably the plasticizer is chosen from trioctyl trimellitate, dioctyl terephthalate or dioctyl phtalate.

In a further embodiment of the fourth aspect of the invention said flexible tube is characterized in that the styrene-butadiene block copolymer exhibits a shore A hardness in the range of 80 to 90.

In a further embodiment of the fourth aspect of the invention said flexible tube is characterized in that the styrene-butadiene block copolymer comprises at least one, preferably two or more, polystyrene block(s) and at least one randomized poly(styrene-co-butadiene) block.

In a further embodiment of the fourth aspect of the invention said flexible tube is characterized in that the styrene-butadiene block copolymer has an overall styrene content of 20% to 80% by weight, preferably 25 to 75% by weight, more preferably 40 to 70% by weight, e.g. 60% by weight.

In a further embodiment of the fourth aspect of the invention said flexible tube is characterized in that the styrene block copolymer comprises an Order-Disorder-Transition Temperature of above 140° C. to 220° C.

In a further embodiment of the fourth aspect of the invention said flexible tube is characterized in that the superimposed layer comprising the styrene-butadiene block copolymer has a thickness of 5 to 200 µm, preferably 15 to 180 µm, more preferably 20 to 160 µm, more preferably 30 to 150 µm.

In a fifth aspect of the invention it has been found that the problem according to an aforementioned object of the invention is solved by a combination comprising at least one tube connection part, adapted to accommodate a flexible tube and at least one flexible tube according to any embodiment of the fourth aspect of the invention.

In a further embodiment of the fifths aspect of the invention said combination is characterized in that tube connection part comprises a sleeve adapted to form an overlapping region between said tube connection part and said tube, and wherein an adhesion promoting agent is deposited on at least a subsection of a surface of said sleeve.

In a further embodiment of the fifths aspect of the invention said combination is characterized in that tube connection part comprises a sleeve adapted to form an overlapping region between said tube connection part and said tube, and wherein an adhesion promoting agent is deposited on at least a subsection of a surface of said sleeve wherein the adhesion promoting agent comprises a styrene-butadiene block copolymer.

In a sixth aspect of the invention it has been found that the problem according to an aforementioned object of the invention is solved by a fluid processing cassette for processing therapeutic or bodily fluids comprising at least one tube according to any embodiment of the fourth aspect of the invention or which comprises a combination according to any embodiment of the fifth aspect of the invention.

BRIEF DESCRIPTION OF THE FIGURES

The invention is further illustrated by FIGS. 1 to 4

DETAILED DESCRIPTION OF THE INVENTION

Figure 1A:
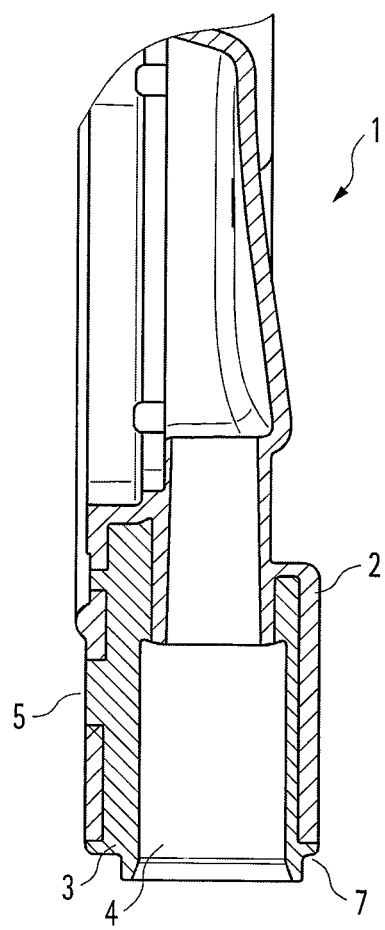
FIG. 1a shows a cross sectional view in axial direction of a tube connection part according to an embodiment of the invention wherein a tube connection part is shown capable to accommodate a flexible tube made from a material comprising polyvinyl chloride to form a tube connection.

The present invention might be understood more readily by the reference to the following detailed description of the invention.

In the context of the present invention the term "tube connection" relates to an assembly wherein a tube connection part accommodates a flexible tube. The tube comprises a conduit for guiding fluids through it and the connection part also comprises a conduit for guiding fluids through it. Tube connection in this respect means that tube and connection part are joint together to form one communicating conduit for guiding fluids through it.

In the context of the present invention the term "tube connection part" relates to a part which is capable to form a tube connection as defined above. In an embodiment those tube connection parts are made from a plastic material or are made rigid or are made from a rigid plastic material. The term "rigid" in this respect means that the connection part is more or less resistant to bending. The term "rigid plastic" means that respective parts, i.e. the tube connection part, are made from plastic materials which provide a glass transition temperature that is above the ambient use temperature of the respective part, i.e. the tube connection part. Thus the term "tube connection part made from a rigid plastic material" is meant to appear as stiff building units. In opposite to flexible building parts, i.e. flexible tubes, a deformation of those rigid plastic connection parts is in general irreversible and will destroy its functionality.

In the context of the present invention the term "sleeve" refers to a geometry which is derived from a cylinder surface. Within the terminology of the present invention said sleeve comprises a inner cavity with an inner surface and an outer surface. A contact between a sleeve and a flexible tube according to the invention might be performed in that the tube is inserted into the sleeve. In this arrangement the outer surface of the tube is adjacent to the inner surface of the sleeve. The sleeve is then regarded to be a part of a female tube connection part. In an alternative embodiment the sleeve may be inserted into the lumen of a respective tube. In this arrangement the inner surface of the tube is adjacent to the outer surface of the sleeve. The sleeve is then regarded to be a part of a male connection part.

In the context of the present invention the term "adhesion promoting agent" relates to any agent that is capable of promoting the adhesion between two parts and which comprises a polystyrene-butadiene block copolymer. This agent is particularly useful in promoting the adhesion of materials comprising PVC and those comprising polypropylene (PP).

In the context of the present invention the term "styrene-butadiene block copolymer" (hereinafter SBC) relates to a block copolymer. Block copolymers consist from at least two different monomers which are not statistically distributed over the polymer chain length but are allocated to at least two respective blocks within the polymer chain. Block copolymers and their way of manufacture are well-known to those skilled in the art and are commercially available. The different blocks are covalently bound to each other to form one polymer chain. In respect of the mentioned styrene-butadiene block copolymer a first block consists almost exclusively of styrene monomer units. A second block consists almost exclusively of butadiene monomer units. However a low percentage of a random co-monomer like styrene may be included into the butadiene block. Defining the polymer chain from its monomer units shall mean that polymerizable reactive sites of the respective monomer are not present anymore in the polymer chain. In this respect a styrene monomer unit will appear as a phenyl-ethyl group and the butadiene monomer will appear as a butyl group in the polymer chain. In preferred embodiments the styrene-butadiene block copolymer is defined by a styrene block and a butadiene block wherein the butadiene is polymerized in a 1,4 fashion, that means that C1 Atom and C4 Atom of the butadiene repeating unit are covalently bound to the respective next monomer unit.

In the context of the present invention the term "fluid processing cassette module" relates to a functional unit for processing bodily fluids like blood or therapeutic fluids like dialysis fluids for the treatment of a respective patient during a therapeutic treatment session. Within the understanding of the present invention such modules designated to fluid processing cassette modules irrespective whether one or more tubes for conveying fluids are connected to the respective fluid processing cassette module.

In the context of the present invention the term "tube" relates to a tubular conduit for conveying fluids from a fluid source to a place of fluid processing, injection or drain. In a main understanding the term "tube" refers to a cylindrical shape which extends in a longitudinal direction which is also referred to as an axial direction. A perpendicular cut to the axial direction will create a cross section of the tube which provides a circular shape. A tube as referred herein comprises at least one lumen which is normally located in a centered position of the circular view of said cross section. However within the gist of the present invention also tubular shapes with a non-circular cross section are herewith also included. In this respect said cross section may also have an elliptical, a polygon, or lip shape.

Flexible in this respect means that respective a tube can be bent without breakage to a minimum radius. The minimum radius is defined to a radius upon which the tube kinks and the inner lumen occludes. In this respect flexible means that the occlusion is reversible and the lumens opens again by a restoring force of the tube when releasing the tube from its bended shape.

The "term flexible PVC tube" relates to an understanding of a tube that is made from a material comprising polyvinyl chloride. Within the understanding of the present invention the tube may consist solely of a PVC material or may be a blend of PVC and other auxiliaries.

In the context of the present invention the term "protruding rib" relates to an embossed shape in a section of a respective building component. The term rib relates to a shape which is longer in its longitudinal direction than wide and whose height of protrusion is smaller than its longitudinal extension. Those ribs might be shaped rectangular or curved or elliptical. According to the invention any shape may be envisioned as long as its effect contributes to the present invention.

In the context of the present invention the term "dove tail" refer to a certain shape of the protruding ribs which means that a cross sectional cut perpendicular to the longitudinal extension of said ribs exhibit the dove tail shape. The term "dove tail" is well known expression in mechanical engineering. At least the expression "dove tail" within the present invention is meant to provide a trapezoidal shaped figure.

In the context of the present invention the term "bushing" refers to a flexible cylindrical shape which in general is made from a plastic film material. A bushing may have a tubular shape. As meant herein a bushing is meant to be wrapped over or into cylindrical shaped articles like a tube end section or the cavity of a sleeve.

In the context of the present invention the term "superimposed" means that at least a part of the adhesion promoting agent is deposited onto the flexible tube of the present invention. In this respect the deposition can be in any form like irregular, sputtered, shaped, patterned, covered or continuous layered as long as it promotes the adhesion between the flexible tube and the tube connection part as disclosed herein.

As referred herein a tube connection is formed by a tube connection part and a flexible tube which is a medical tube and is made from a material comprising polyvinyl chloride (hereinafter PVC). Tubes for conveying medical fluids are widely known in the art. Regarding the field of dialysis in particular the field of hemodialysis several kind of tubes are essential to perform a therapeutical treatment session. Regarding a fluid processing cassette module for processing therapeutic or bodily fluids different kind of tubes are connected to the cassette module. Among those different tubes can be found:

blood tubing which typically may have an outer diameter of about 10.2 mm, an inner lumen diameter of 7.2 mm and a wall thickness of about 1.5 mm. These tubes convey p.e. patient blood to a blood processing unit, p.e. a dialyzer.

dialysis fluid tubing which are intended to convey fresh and used dialysis fluids heparin tubing which are intended to deliver heparin to the extracorporal blood circuit in hemodialysis to prevent blood coagulation.

Pump tubing which is intended to provide a pumping means by a peristaltic treatment of said pump tubes. Said peristaltic treatment is caused by p.e. by a pump actor in form of an rotor which comprises rollers at the rotor end sections to compress the pump tube in a peristaltic way. These tube sections are especially used to maintain blood and dialysis fluid flow in the extracorporal treatment of hemodialysis. Pump tubes typically exhibit an inner lumen diameter of 8 mm, a wall thickness of 2.1 mm and complete diameter of 14.2 mm In a first aspect the invention refers to a tube connection part adapted to accommodate a flexible tube made from a PVC material. The tube connection part is characterized in that it forms a sleeve part to accommodate a flexible tube. According to the first aspect of the invention the tube connection comprises at least a sleeve which comprises an adhesion promoting agent deposited on said sleeve, wherein the adhesion promoting agent comprises a styrene-butadiene block copolymer.

A tube connection as referred herein is performed by inserting a tube onto or into a receiving section of the sleeve of said tube connection part. It is essential that both, the flexible PVC tube and the sleeve of the tube connection part form an overlapping region when they are engaged to each other. The overlapping region forms a contacting area between the flexible PVC tube and the sleeve by which a binding of the tube connection can be achieved. The inventors have found that by depositing an adhesion promoting polymer made from a SBC onto a surface of the sleeve of the tube connection part adhesion between the sleeve and the flexible PVC tube is dramatically enhanced. Thus it was even possible to generate a resilient joint which is strong enough to resist a mechanical impact which is induced for examples on pump tube sections caused by the pump actuation of roller pump actors.

The inventors further found that it is preferred that flexible PVC tube and tube part form a press fit. That means that either the sleeve of the tube connection part or the PVC flexible tube shall be produced in a slight undersize. When engaging those flexible PVC tube onto or into said sleeve of the tube connection part a force has to be applied to create the tube connection. This will put the flexible PVC tube under a pretension so that under gluing conditions a more close material contact is created between the tube connection part and the flexible PVC tube towards the adhesion promoting agent, SBC, deposited on the sleeve.

According to another embodiment of the first aspect of the invention the sleeve of the tube connection part comprises protruding ribs. The protruding ribs extend in axial direction of the overlapping region between flexible tube and rigid connecting part. The axial direction of the overlapping region is meant to be the longitudinal direction of a flexible tube, when inserted into the tube connection part being in an unbent shape.

When the adhesion promoting agent is deposited onto the sleeve surface which form the protruding rib structure a mechanical hold point is formed which holds. It was found that those protruding ribs improve the strength of a joint which is developed towards an inserted tube. It is believed that the increase of stability is caused by the press fit of the tube when inserted to the tube material of the fluid processing cassette. The pretention of an inserted tube also applies a tension on the adhesion promoting agent which is deposited on the protruding ribs. Thus, the mechanical interference between protruding ribs and deposited adhesion promoting agent is based on an additional force fitting connection enhancing the overall joint strength.

In a preferred embodiment of the first aspect of the invention the protruding ribs are provided in a dove tailed shape. That means that a cross sectional cut perpendicular to the longitudinal extension of said ribs exhibit the dove tail shape. It was found that the mechanical interaction between dove tail shaped ribs and the adhesion promoting agent is enhanced. Corresponding tube connections made from a tube connection part comprising a sleeve with dove tail shaped ribs and, an adhesion promoting agent SBC and a flexible tube made from a material which comprises PVC provide an enhanced resilience and are preferred.

In another embodiment of the first aspect of the invention a mechanical hold point between the sleeve of the tube connection part and the adhesion promoting SBC is achieved by forming recesses which extend inwardly from an outer surface of said sleeve which are preferably present in the overlapping region which is formed between the sleeve of the tube connection and a flexible tube. In such an embodiment deposited styrene-butadiene block copolymer can fill out the recesses and form a mechanical hold point to enhance the interaction between tube connection part and the SBC which will also increase the tube connection resilience The SBC might be deposited onto the sleeve surface by various techniques. In one embodiment the SBC id deposited by overmolding the sleeve of the tube connecting part in a 2-component injection molding process. The process of overmolding of plastic parts is well known in the art. After the preparation of the overmolded tube connection part a flexible PVC tube can be inserted into the connection part to form an overlapping region between the sleeve of the tube connection part and the flexible PVC tube. At least the overmolding is performed in a subsection of a surface of said sleeve. Therefore in one embodiment of the first aspect of the invention the SCB deposition is achieved by overmolding.

A joint between the modified tube part and the flexible PVC tube might be achieved by gluing. When gluing is a preferred process for binding the flexible PVC tube and the tube connection together a by means of a SBC gluing is performed using a solvent like "Tetramek" which is a solvent mixture obtained from Tetrahydrofuran and Methyl Ethyl Ketone. It was found that strong joints is formed by gluing was formed.

Gluing can be performed according to a process wherein in a first step the tube seat comprising the adhesion promoting agent was wetted with above mentioned Tetramek solvent. In a second step the tube end section is immersed in the same solvent for about 5 seconds. Following the tube end section is inserted into or onto the tube seat. The tube is blocked for at least 20 seconds in its position to form the glued tube connection.

Another option is to interpose the adhesion promoting styrene-butadiene block copolymer by means of a bushing which is wrapped between the flexible PVC tube and the tube part. Another way is to use a flexible PVC tube which is modified on one or both outer surfaces areas with the said styrene-butadiene block copolymer In still another embodiment of the first aspect of the invention the mechanical interaction of tube connection part and the adhesion promoting SBC is enhanced by SPC forming an outer collar on the sleeve of the tube connection. The outer collar provides an additional mechanical support structure to fix the adhesion promoting agent which is may be deposited by an overmolding process of a SBC to the structure of the sleeve of the tube connection part.

In still another embodiment of the first aspect of the invention the adhesion promoting agent forms in one part of the tube connection part a front surface flange. The surface flange forms faces to the end section of a inserted tube. The flange is parallel to a perpendicular cut of the longitudinal direction of the tube connection part in particular perpendicular the longitudinal direction of the overlapping region.

In still another embodiment of the first aspect of the invention the adhesion promoting agent is characterized in that the content of polystyrene blocks in the SBC ranges between 5% to 35%, by weight. Preferably the content of polystyrene blocks in the SBC ranges from 7 to 25%, preferably ranges from 10 to 20%. In this respect a styrene block content below 5% of the overall SBC weight has shown to provide weak tube connections. On the other hand a styrene block content of above 35% has shown to be problematic in the manufacturing of a tube connection according to the invention.

According to another embodiment of the first aspect of the invention the inventors found that the overall styrene content, i.e. the styrene present in the polystyrene blocks and styrene present as a random co-monomer in the butadiene block, influences the interaction between the sleeve of the tube connection part and a flexible tube. In this respect a preferred overall styrene content was found to be in the range of 20 to 80%, preferably 25% to 75%, more preferably 40 to 70%.

In one embodiment of the first aspect of the invention it is an object to mediate a good adhesion bonding between a tubing, like a flexible PVC tubing, and the tube connection part via the adhesion promoting agent SBC it is preferred to choose a SBC which is able to fit closely to the sleeve of tube connection part of the fluid processing cassette module on one side and to the a flexible tubing on the other side. By providing an appropriate hardness of the styrene-butadiene block copolymer surface roughness of the sleeve of the tube connection part and the flexible PVC tube can be compensated such that the interposed styrene-butadiene block copolymer comes in an even closer surface contact with the adjacently disposed tube. The close surface contact of the sleeve of the tube connection part and the adhesion promoting agent has a positive impact on the joint strength. In this respect a shore hardness of shore A=80 to 90 has been shown to be advantageous. (measured according to standard ISO 868)

According to a further embodiment of the first aspect of the invention it was further found to be important to adapt the rheological and polarity properties of the adhesion promoting agent, i.e. the SBC, to find an advantageous interaction tendency of the styrene-butadiene block copolymer with the tube connection part of the fluid processing cassette module. Both, rheological and polarity properties can be influenced by the chemical heterogeneity and architecture of the polymer chain used as an adhesion promoting agent. Rheological property can be influenced via the chain stiff polystyrene block in the styrene-butadiene block copolymer. Polarity of said polymer chains can be influenced by adapting the amount of randomly distributed styrene repeating units incorporated into the flexible polybutadiene block of the styrene-butadiene block copolymer. To combine those two influences an adhesion promoting agent which comprises a styrene-butadiene block copolymer built from a polystyrene block and a block of a random copolymer of butadiene and styrene is preferred. It is even more preferred that the polystyrene-butadiene block copolymer comprises polymer chains with at least two polystyrene blocks and at least one block made of a random copolymer of butadiene and styrene.

Polymer materials made from aforementioned polymer architecture and chemistry are known to form phase separations on a micro- or nanoscopic scale. The micro- or nanostructure of such polymer material is responsible for elastomeric, plastic, and rheological characteristic. To preserve such properties even at elevated temperature which might occur during heat sterilization processes, it is important to choose an adhesion promoting agent whose micro- or nanostructure is resistant even at temperatures of autoclaving heat sterilization which is commonly performed at 121° C. Therefore in one embodiment of the first aspect of the invention the tube connection part is further characterized by an adhesion promoting styrene-butadiene block copolymer that comprises an Order-Disorder-Transition Temperature of above 140° C. The Order-Disorder Transition Temperature can be determined by rheological measurement. It is defined as the Temperature where the shear modulus (G') shows an abrupt change (Kim et. al.; Macromolecules 1998, 31, 4045, standard ISO 6721)

A maximum of the lower limit of the Order Disorder Transition Temperature is given by thermic decomposition processes of the polymer. Regarding SBC's as used for embodiments according to the invention a thermic stability of above 220° C. does not provide any benefit for the invention.

The sleeve of said tube connection may form a female or a male part to form together with a flexible a tube connection according to one aspect of the invention. In one embodiment it is preferred that the sleeve forms a female part as resilience of the tube connection is higher. A tube connection can be formed by inserting a flexible tube, for example a flexible PVC tube into the sleeve of the shaped tube connection part. The styrene-butadiene block copolymer material adhered to the tube connection part of the fluid processing cassette module thereby comes in contact with the outer surface of the tube. It has been proofed that tube connections with higher joint strength can be achieved if the sleeve of the tube connection part is shaped as a female connection part. By this means the overlapping surface area is larger than in tube connection where the tube connection part forms a male part.

In one embodiment of the first aspect of the invention it is preferred that the tube connection part is made from or comprises a polypropylene (PP) polymer material. In alternative embodiments the tube connection part may be either made from a copolymer of propylene and ethylene (PPE). Polypropylene and random Copolymers of propylene and ethylene are widely used and are preferred materials in the production of medical disposables. Polypropylene materials are translucent, which is an important feature in the processing of medical fluids because major irregularities of processed fluids, like coagulation of blood components or precipitation of salts, may be detected visually. Further it was found that said polypropylene materials provide a good compatibility to said adhesion promoting agent which comprises styrene-butadiene block copolymer so that PP materials or PPE copolymer materials proved to be good starting materials for overmolding processes as described herein further.

In a preferred embodiment of the first aspect of the invention the tube connection part is made rigid. In case the tube connection is made in a rigid way the tube connection might be fixed to machine parts by mechanical means. This becomes an important feature in particular when a machine actuation is intended to interfere with the flexible tube of the tube connection or the rigid tube connection part. For example the rotor of a roller pump may act onto a pump tube section which is a part of a tube connection according to the invention.

In a second aspect the invention refers to an assembly comprising the tube connection part according to any embodiment of the first aspect of the invention and a flexible tube which is made from a material which comprises PVC.

A tube connection as referred herein is performed by inserting the tube onto or into a receiving section of tube connecting part. It is essential that both, the flexible PVC tube and the tube connection part form an overlapping region when they are engaged to each other. The overlapping region forms a contacting area between the flexible PVC tube and the tube connecting part by which a binding of the tube connection can be achieved. The inventors have found that by way of interposing an adhesion promoting polymer made from a styrene-butadiene block copolymer adhesion between tube part and flexible PVC tube is dramatically enhanced. Thus it was even possible to generate a resilient joint which is strong enough to resist even huge mechanical impact which is induced onto said pump tube sections caused by the pump actuation of the roller pump actors.

In one embodiment of the second aspect of the invention the flexible PVC tube is made from a plasticized material. Among a row of used plasticizers for PVC it has been found that alkyl esters of trimellic acid, terephtalic acid or phtalic acid are preferred because of their good compatibility to the adhesion promoting agent poly styrene-butadiene block copolymer and their hemocompatibility in PVC blood tubing. It has been further found that the choice of the right plasticizer material is crucial for the formation of a tube connection according to the invention. Several other plasticizer materials destabilized the tube connection. It was found that PCV plasticizer also solubilize the SBC and therefor reduces the adhesion force in the overlapping region of the tube connection. It was found that a trioctyl ester of the trimellic acid, a dioctyl ester of terephtalic acid, a dioctylester of phtalic acid provided the preferred adhesion performances. One of the preferred plastizier is trioctyl trimellitate in particular tris (2-ethylhexyl) trimellitate.

In a third aspect the invention refers to a fluid processing cassette module for processing therapeutic fluids comprising at least one tube connection part according to any embodiment of the first aspect of the invention or comprising an assembly according to any embodiment of the second aspect of the invention.

In one embodiment of the third aspect of the invention the fluid processing cassette comprises a plurality of tube connection parts. It has been found that processes for manufacturing of overmolded tube connection parts can be simplified by interconnected at least two tube connection parts with one conduit for evenly distributing a polymer melt stream to the at least two rigid connecting parts. Regarding the complex structures of fluid processing cassette modules the amount of necessary polymer melt injection ports can be reduced.

In another embodiment of the third aspect of the invention the tube connection part and the fluid processing cassette module form an integral unit. Such a construction benefits from the production advantages wherein the fluid processing cassette module and tube connection part can be produced in one injection molding process. Additionally in a consecutive injection molding step the overmold of the adhesion promoting agent comprising styrene-butadiene block copolymer is applied to the tube connection parts. In this respect the term "integral" means, as mentioned above, that fluid processing cassette module and tube part cannot be separated without destroying the functional purpose of the fluid processing cassette module.

In a further embodiment of the third aspect of the invention the fluid processing cassette module is made from a polypropylene (PP) polymer, in an alternative the cassette is made from a copolymer made from propylene and ethylene (PPE). Polypropylene and random Copolymers of propylene and ethylene are widely used and are preferred materials in the production of medical disposables. Polypropylene materials are translucent, which is an important feature in the processing of medical fluids because major irregularities of processed fluids, like coagulation of blood components or precipitation of salts, may be detected visually. Further it was found that said polypropylene materials provide a good compatibility to said adhesion promoting agent which comprises styrene-butadiene block copolymer so that PP materials or PPE copolymer materials proved to be good starting materials for overmolding processes as described herein further.

According to one embodiment of the third aspect of the invention the fluid processing cassette module comprises the tube connection parts, which form female connection parts. A tube connection can be formed by inserting a flexible tube, p.e. a flexible PVC tube into a sleeve of the shaped tube connection part. The styrene-butadiene block copolymer material adhered to the tube connection part of the fluid processing cassette module is accessible to an outer surface of the tube. It has been proofed that tube connections with higher joint strength can be achieved if the rigid connecting part on the fluid processing cassette module is shaped as a female connection part. By this means the overlapping surface area is larger than in tube connection where the tube connection part forms a male part In a fourth aspect the invention refers to a flexible tube comprising a material from polyvinyl chloride and a superposed material comprising an adhesion promoting material which comprises a styrene-butadiene block copolymer wherein the superimposed material from styrene-butadiene block copolymer covers at least a part of a tube surface. At least the styrene-butadiene block copolymer is superimposed on end sections of said flexible PVC tube so that by engaging the tube with a corresponding connection part the adhesion promoting agent becomes interposed in an overlapping region of a corresponding connection part and the flexible PVC tube.

In certain embodiments of the fourth aspect of the invention the flexible tube comprising a material from a polyvinyl chloride is a tube that is made from PVC and a plasticizer. In this respect the term "flexible tube comprising a material from polyvinyl chloride" does also comprise the term of a "flexible PVC tube".

In still other embodiments of the fourth aspect of the invention the adhesion promoting agent comprising a material from a styrene-butadiene block copolymer is meant to consist of a styrene-butadiene block copolymer.

In one embodiment of the fourth aspect of the invention the superimposed adhesion promoting material is applied to the outer surface of said flexible tube. This makes it possible to use a female complementary connection part for a tube connection with said flexible PVC tube. In this respect is advantageous In one embodiment of the fourth aspect of the invention the superimposed adhesion promoting material comprising a styrene-butadiene block copolymer forms a continuous layer which fully covers the outside surface of the tube at least in the area where the adhesion promoting material is applied to and at least in the area where an overlapping with a tube connection part is expected when the tube is inserted in such a tube connection part.

In another embodiment of the fourth aspect of the invention the continuous superimposed adhesion promoting material comprising styrene-butadiene block copolymer can be produced by coextrusion of a multilayer tube. The main tube layer is thereby formed by the PVC material. A second layer may be formed by the adhesion promoting agent, which comprises the SBC. By coextrusion the coextruded tube is obtained from two polymer melts which are the PVC melt and the styrene-butadiene block copolymer melt. The two melts are extruded via an extrusion nozzle to form a two layered tube. As both, PVC and styrene-butadiene block copolymer are contacted in the melt phase the adhesion between the PVC tube layer and styrene-butadiene block copolymer layer is extraordinary high.

The SBC may be even applied by other techniques onto the flexible PVC tube surface. Other techniques may comprise to superimpose a bushing containing the styrene butadiene block copolymer onto the outer surface of the flexible PVC tube.

Still other methods may comprise to apply the styrene-butadiene block copolymer onto the outer surface of the flexible PVB tube by dip coating.

According to one embodiment of the fourth aspect of the invention the flexible PVC tube is made from a plasticized material. Among a row of used plasticizers for PVC in the art it has been found that alkyl esters of trimellic acid, terephtalic acid or phtalic acid are preferred because of their good compatibility to an adhesion promoting agent like poly styrene-butadiene block copolymer and their hemocompatibility in PVC blood tubing. It has been further found that the choice of the right plasticizer material is crucial for the formation of a tube connection according to the invention. Several other plasticizer materials showed to destabilize the tube connection. It was found that the PCV plasticizer may also solubilize the styrene-butadiene block copolymer and may reduce the adhesion force in overlapping region of the tube connection.

In another embodiment of the fourth aspect of the invention it has been an object to find a PVC material which is suitable to be used under the requirements of medical tubes but which is on the other hand not detrimental to the strength of the tube connection. It was found that a trioctyl ester of the trimellic acid, a dioctyl ester of terephtalic acid, a dioctylester of phtalic acid showed promising adhesion performances. One of the preferred plastizier is trioctyl trimellitate in particular tris (2-ethylhexyl) trimellitate.

In another embodiment of the fourth aspect of the invention it was found to mediate a good adhesion binding between said flexible PVC tubing and a tube connection part which might be a tube connection part made from PP. It is preferred to choose flexible PVC tube with a superimposed polystyrene-butadiene block copolymer which is able to fit closely to a complementary tube connection part. This can be achieved by providing a styrene-butadiene block copolymer with an appropriate hardness. In particular surface roughness present in the surface of the tube connection part can be compensate such that the interposed styrene-butadiene block copolymer comes in a close contact with the adjacent connection parts. The hardness of the superimposed styrene-butadiene block copolymer may have a positive impact on the joint strength which is obtained after the gluing process. In this respect a shore hardness of shore A=80 to 90 has been shown to be advantageous (measured according to standard ISO 868).

In another embodiment of the fourth aspect of the invention it was found to be important to adapt the rheological and polarity properties of the adhesion promoting agent, i.e. the styrene-butadiene block copolymer, which is superimposed onto the surface of the flexible PVC tube. Both, rheological and polarity properties are influenced by the chemical heterogeneity and architecture of the polymer chain used as an adhesion promoting agent. Rheological properties can be influenced by the chain stiff polystyrene block in the styrene-butadiene block copolymer. Polarity of said polymer chains can be influenced by adapting the amount of randomly distributed styrene repeating units incorporated into the flexible polybutadiene block of the styrene-butadiene block copolymer. To combine those two influences an adhesion promoting agent which comprises a styrene-butadiene block copolymer built from a polystyrene block and a block of a random copolymer of butadiene and styrene is preferred. It is even more preferred that the polystyrene-butadiene block copolymer comprises polymer chains with at least two polystyrene blocks and at least one block made of a random copolymer of butadiene and styrene.

In still another embodiment of the fourth aspect of the invention the adhesion promoting agent is characterized in that the content of polystyrene blocks in the SBC ranges between 5% to 35%, by weight. Preferably the content of polystyrene blocks in the SBC ranges from 7 to 25%, preferably ranges from 10 to 20%. In this respect a styrene block content below 5% of the overall SBC weight has shown to provide weak tube connections. On the other hand a styrene block content of above 35% has shown to be problematic in the manufacturing of a tube connection according to the invention.

According to another embodiment of the first aspect of the invention the inventors found that the overall styrene content, i.e. the styrene present in the polystyrene blocks and styrene present as a random co-monomer in the butadiene block, influences the interaction between the sleeve of the tube connection part and a flexible tube. In this respect a preferred overall styrene content was found to be in the range of 20% to 80%, preferably 25% to 75%, more preferably 40 to 70%.

Polymer materials made from aforementioned polymer architecture and chemistry are known to form phase separations on a nanoscopic scale. The micro- or nanostructure of such polymer material is responsible for elastomeric, plastic, and rheological characteristic. To preserve such properties even at elevated temperature which might occur during heat sterilization processes, it is important to choose an adhesion promoting agent whose nano/-microstructure is resistant even at temperatures of autoclaving heat sterilization which is commonly performed at 121° C. Therefore the present invention is further characterized by a adhesion promoting styrene-butadiene block copolymer that comprises an Order-Disorder-Transition Temperature of above 140° C.

In a fifth aspect the invention refers to an assembly of a fluid processing cassette module for processing therapeutic or bodily fluids comprising at least one tube connection part and at least one a flexible tube made from a material comprising polyvinyl chloride, wherein the tube connection between fluid processing cassette module and the said flexible PVC tube is formed via a tube connection part placed on the fluid processing cassette module and the flexible PVC tube wherein the tube connection part may be any tube connection part and said flexible PVC tube is a tube according to any embodiment of the fourth aspect of the invention.

In a further embodiment of the fifth aspect of the invention the tube connection is formed via a tube connection part placed on the fluid processing cassette module and the flexible tube made from a material comprising PVC wherein the tube connection part is a connection part according to any of the embodiments of the first aspect of the invention and the flexible PVC tube is a tube according to any embodiment of the fourth aspect of the invention.

In a further embodiment of the fifth aspect of the invention the tube connection is formed via a tube connection part placed on the fluid processing cassette module and a flexible tube made from a material comprising PVC wherein the tube connection part is a connection part according to any of the embodiments of the first aspect of the invention and the flexible PVC tube is a tube according to any embodiment of the fourth aspect of the invention and the fluid processing cassette module is a module according to any embodiment of the third aspect of the invention.

Detailed Description of the Figures and Embodiments

The present invention might be understood more readily by the reference to following detailed description of the FIGS. 1 to 4 and its corresponding embodiments. It is understood here the present invention is not comprehensively defined by the features given by figures. The skilled person in the art will understand that the figures represent certain embodiments within the scope of the invention from which other embodiments of the invention can be achieved.

FIG. 1a shows an embodiment of a tube connection part (1) according to a, second, third or fifth aspect of the invention. The figure shows a cross sectional view of a female tube connection part according to a plane cut which is parallel to the longitudinal direction of the of the tube connection part. The tube connection part is constructed from rigid side walls (2) defining a inner cavity of a sleeve adapted accommodate a tube end section in tube seat (4) which represents an overlapping region between sleeve and tube end section. In the present case the material of the tube connection part is a material which can be formed by injection molding into the appropriate shape that is suggested in FIG. 1a. In this respect an appropriate material is a PP, preferably the PP is a polypropylene that is resistant to an e-beam sterilization process. In this respect a preferred polypropylene is sold by LyondellBasell under the trade name Purell HP371P.

In the respective embodiment of FIG. 1a the tube seat is further formed by a layer (3) which is formed by an adhesion promoting agent which comprises a SBC. According to the present embodiment of FIG. 1a the adhesion promoting agent is applied by an overmold process to fill out said cavity of the tube connection part and form a tube seat (4) in a overlapping region.

Preferably the overmolding of the tube connection part made from the aforementioned PP material is done in a second step of two consecutive steps of a 2-component injection molding. In the first position the tube connection part made from PP is molded into shape in a mold cavity of a molding tool. Then the mold tool opens. An inner plate rotates and brings the tube connection part (blocked inside the plate) in the second position. The mold tool closes again and tube seat pins of a second position enter into the tube connection part. The adhesion promoting agent is then injected via the recess (5) in this second position. Then the mold tool opens again and the tube connection part is expelled. The tube connection part of FIG. 1 is further characterized by an outer collar which (7) which is produced upon a circumferential edge of the rigid sidewalls of the said tube connection part. This outer collar supports the injected adhesion promoting agent in is position and is responsible for additional mechanical strength. Additional support is provided by the opening (5) which serves as an injection port on the one hand. On the other hand the opening (5) serves as a hold point for the injected adhesion promoting agent. A preferred material for the adhesion promoting material is sold by INEOS Styrolution under the trade name Styroflex 2G66.

Figure 1B:
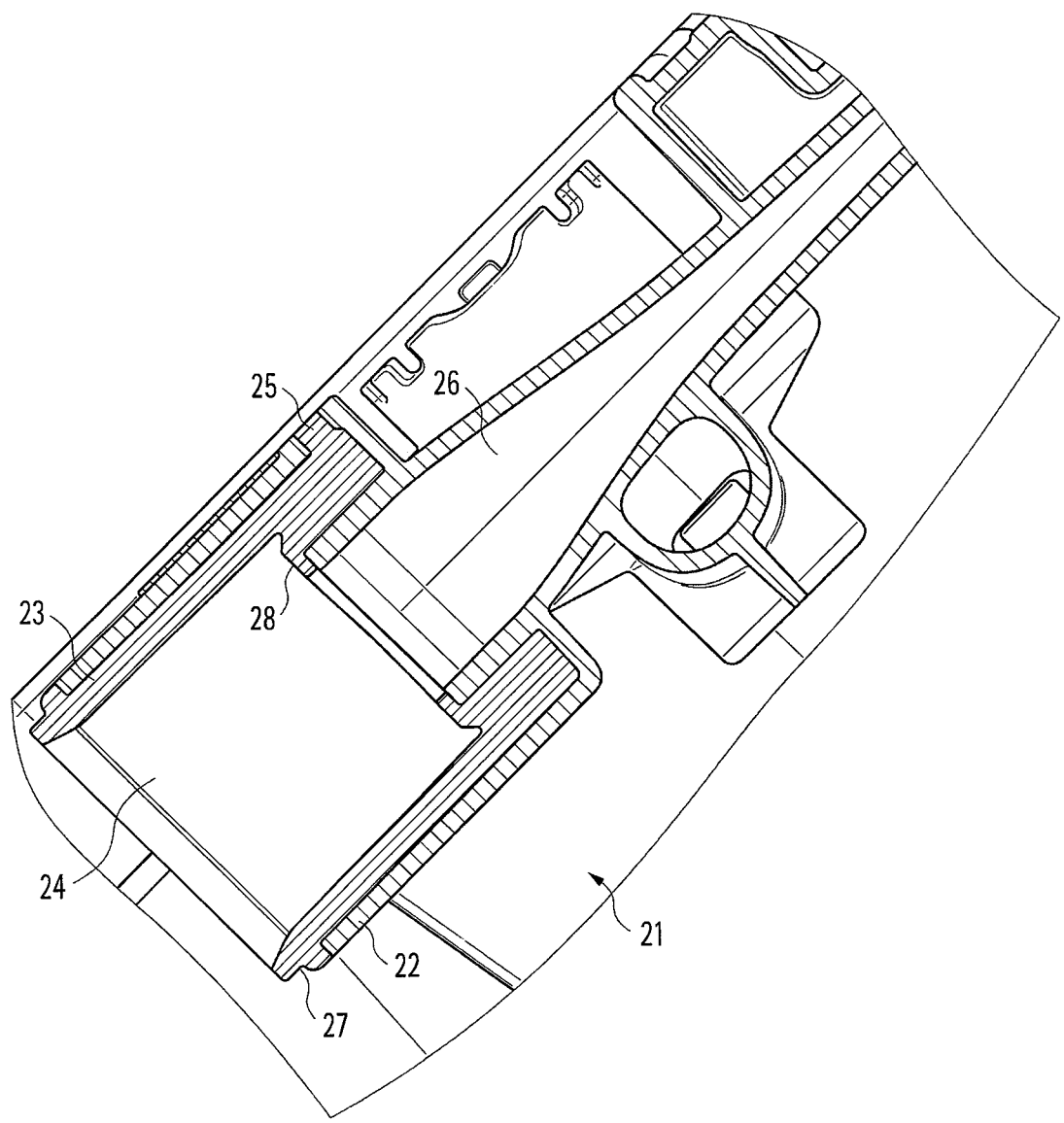
FIG. 1b shows a cross sectional view analog to FIG. 1a according to another embodiment of the invention.

FIG. 1b shows an alternative embodiment according to the first, second, third or fifth aspect of the invention. FIG. 1b shows analog to FIG. 1a a cross sectional view of a female tube connection part according to a plane cut which is parallel to the longitudinal direction of the of the tube connection part. In the present embodiment the tube connection part is adapted to accommodate a pump tube end section which connects with conduit part 26 to form together with the conduit of the pump tube section one communicating conduit upon tube insertion. The tube connection part (21) of FIG. 1b comprises rigid side walls (22), defining an inner cavity of a sleeve, made from PP material, preferably made from aforementioned Purell HP371P. The tube connection part of FIG. 1b further comprises an overmolding (23) made from an adhesion promoting agent which comprises preferably Styroflex 2G66 to accommodate a tube end section in a tube seat that provides the overlapping region (24) between sleeve and tube end section. The adhesion promoting agent may be injected via recess (25) in an overmolding process. The tube connection part is further characterized by an outer collar (27), which is produced upon a circumferential edge of the rigid sidewalls of the said tube connection part. This outer collar supports the injected adhesion promoting agent in is position and is responsible for additional mechanical strength. Additional support is provided by the recess (25) which serves as an injection port on the one hand. On the other hand the opening (5) serves as a hold point for the injected adhesion promoting agent. The tube connection part of FIG. 1b is further characterized by a front surface flange (28) that is arranged perpendicular to the shown cut along the longitudinal direction of said tube connection. By insertion of a tube end section this flange abuts to the end sectional face of said tube.

Figure 2:
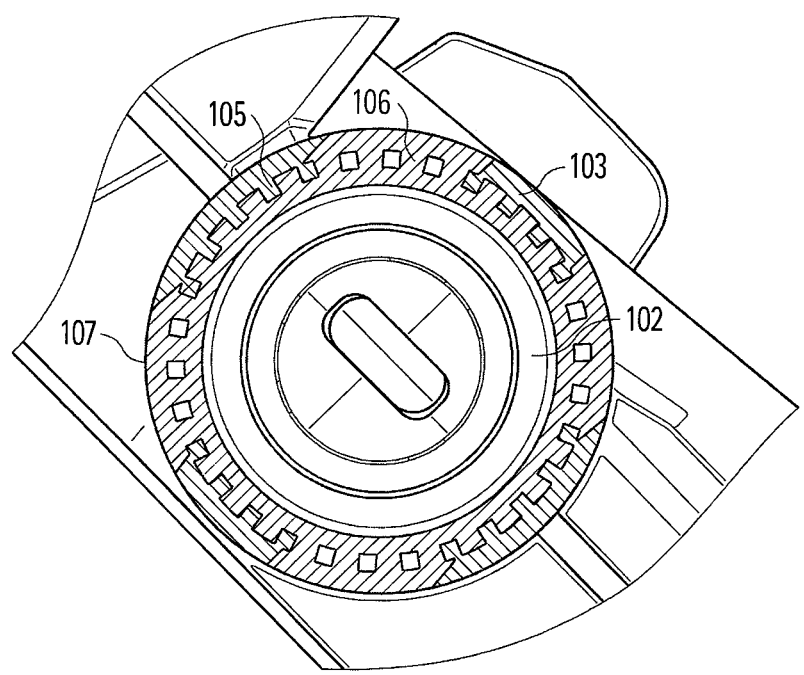
FIG. 2 shows a cross sectional view perpendicular to the longitudinal axis of an assembly of a tube connection part and a flexible tube according to one embodiment of the invention.

FIG. 2 represents another embodiment according to the first, second, third or fifth aspect of the present invention. The figure displays a cross sectional view of a tube connection (101) perpendicular to its longitudinal direction comprising a tube connection part and a tube inserted into it. The figure shows a circular cross section of an inserted tube (102) which is surrounded by continuous layer (106) of an adhesion promoting material which comprises a styrene-butadiene block copolymer. The side walls of the tube connection part (103) are structured to certain shapes of ribs (105). In the respective plane cut shown in FIG. 2 the side walls (103) do not form a continuous surrounding wall. As shown the side walls provide openings (107) which may serve as injection ports or as anchoring recess point to stabilize the adhesion promoting agent in the tube seat position (104).

Figure 3:
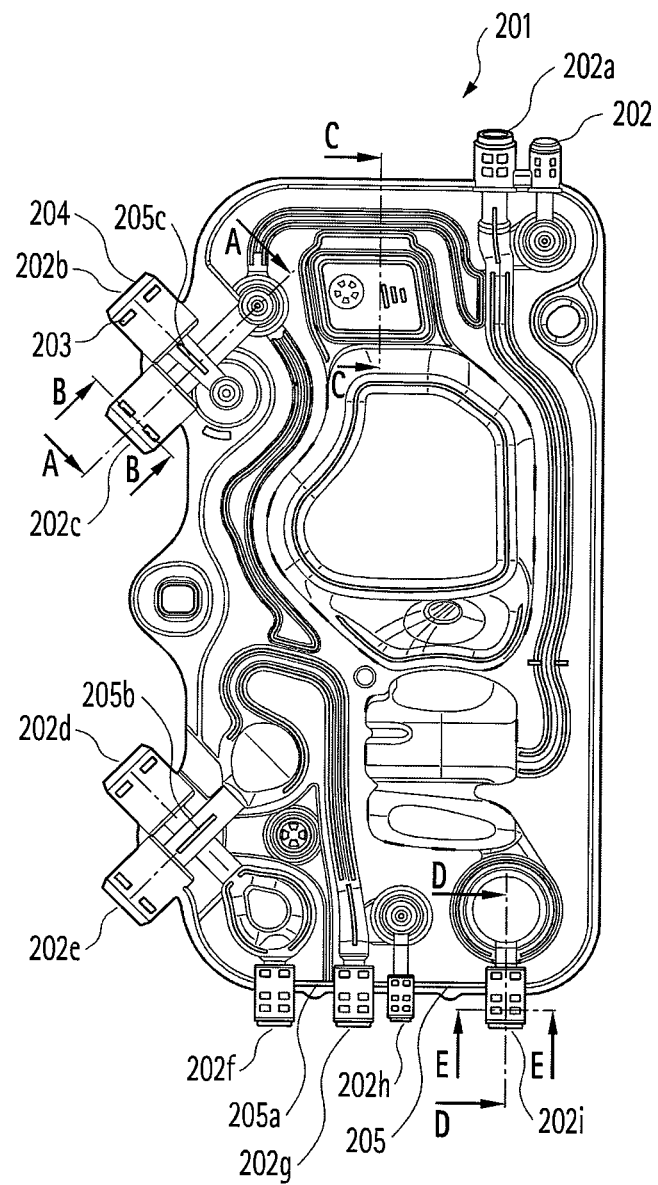
FIG. 3 shows a fluid processing cassette module providing a plurality of tube connection parts, wherein the tube connection parts each are capable to accommodate a flexible tube to form a tube connection according to one embodiment of the invention.

FIG. 3 shows projected view on one side of a schematic representation of an embodiment of a fluid processing cassette module (201) according to the third and fifth aspect of the invention. The fluid processing cassette module represents a functional unit which accommodates a plurality of fluid processing sites. According to the second aspect of the invention the fluid processing cassette module comprises a plurality of tube connection parts (202) to (202i). As can be seen rigid connection parts and cassette module form an integral unit which is obtainable by an injection molding process especially a 2-component injection molding process as explained before. As can be seen from FIG. 3 the tube connection parts are characterized by features also explained before, namely the anchoring recesses (203) and the outer rings (204). The fluid processing cassette is further characterized by slits (205) to (205c) which extend between or combines two tube connections parts. Those slits can be used for the injection of a polymer melt of the adhesion promoting agent and distribution of the injection melt between two tube connection parts. As a consequence it is possible to reduce the amount of injection nozzles necessary to inject the adhesion promoting agent into the tube seat area of a respective in the mold tool.

Figure 4:
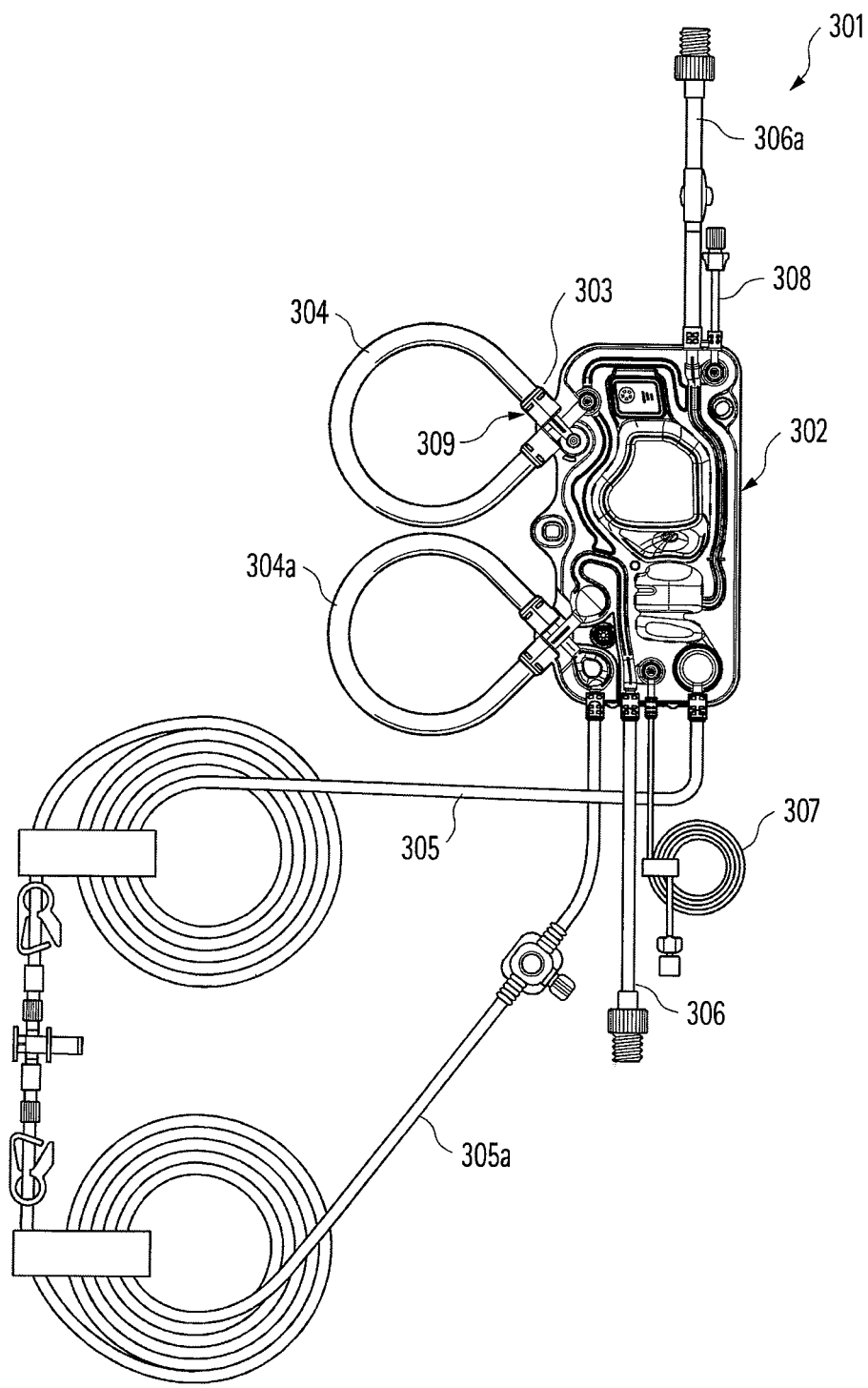
FIG. 4 shows an assembly comprising a fluid processing cassette module comprising a plurality of tube connection parts and a plurality of flexible tubes according to one embodiment of the invention

FIG. 4. shows an embodiments of an inventive assembly (301) according to the third, fourth, and fifth aspect of the invention, comprising a fluid processing cassette module (302), further comprising a plurality of tube connections like connection (303) composed p.e. from tube (304) and a tube connection part 309, further comprising flexible tubes (304), (304a), (305), (305a), (306), (306a), (307), (308). FIG. 4 shows a projected view on one side of a schematic representation of said assembly. The assembly represents a unit for the extracorporal blood treatment of dialysis treatment. The fluid processing cassette module is intended for the blood processing during a hemodialysis treatment session. The assembly is further characterized by a plurality of different tubes which are necessary to maintain the blood treatment session. Those tube are in detail a pump tube loop (304), (304a) for maintaining a fluid stream by peristaltic pump actions, system tubes (305), (305a), (306), (306a) for the conveyance of bodily fluids which may be blood in the represented embodiment, a heparin tube (307) for the administration of an anticoagulant to the extracorporal blood circuit and a venous injection tube (308).

The invention claimed is:

1. A tube connection part adapted to accommodate a flexible tube made from a material comprising polyvinyl chloride, wherein the tube connection part comprises a sleeve adapted to form an overlapping region between the tube connection part and the tube, wherein
    an adhesion promoting agent is deposited on at least a subsection of a surface of the sleeve,
    the adhesion promoting agent comprises a styrene-butadiene block copolymer,
    the sleeve comprises protruding ribs that extend in an axial direction thereof, and
    the protruding ribs are dove tail shaped.

2. The tube connection part according to claim 1, wherein the sleeve comprises at least one recess extending inwardly from its outer surface.

3. The tube connection part according to claim 1, wherein the adhesion promoting agent is deposited as an overmolding on at least a subsection of a surface of the sleeve.

4. A fluid processing cassette module for processing therapeutic or bodily fluids, comprising at least one tube connection part according to claim 3.

5. The fluid processing cassette module according to claim 4, wherein the cassette module comprises a plurality of tube connection parts characterized in that at least two tube connection parts are interconnected by at least one conduit adapted to simultaneously distribute a polymer melt stream comprising a styrene-butadiene block copolymer to the at least two tube connecting parts for the manufacture of the overmolding on at least a subsection of a surface of the sleeve.

6. The tube connection part according to claim 1, wherein the adhesion promoting agent forms an outer collar on the sleeve of the tube connection part.

7. The tube connection part according to claim 1, wherein at least a portion of the adhesion promoting agent forms a front surface flange adapted to accommodate an end face of the tube.

8. The tube connection part according to claim 1, wherein the overall styrene content in the styrene-butadiene block copolymer amounts to 20% to 80% by weight.

9. The tube connection part according to claim 1, wherein the styrene-butadiene block copolymer exhibits an Order-Disorder-Transition temperature of above 140° C. and up to 220° C., or a Shore A hardness in the range of 80 to 90.

10. The tube connection part according to claim 1, wherein the sleeve forms a female or a male connecting part.

11. The tube connection part according to claim 1, which is rigid, or which is made of a plastic material, or which is rigid and made of a plastic material.

12. An assembly comprising the tube connection part according to claim 1, and a flexible tube made from a material comprising polyvinyl chloride, wherein the tube is engaged in the overlapping region of the sleeve of the tube connection part, and the tube is connected to the tube connection part via the adhesion promoting material.

13. The assembly according to claim 12, wherein the flexible tube is made from a material comprising polyvinyl chloride that comprises a plasticizer chosen from the group of alkyl esters of trimellic acid.

14. The tube connection part according to claim 1, wherein the styrene-butadiene block copolymer exhibits an Order-Disorder-Transition temperature of from above 140° C. to 220° C. and a Shore A hardness in the range of from 80 to 90.

* * * * *